United States Patent [19]

Friedman et al.

[11] 4,055,394
[45] Oct. 25, 1977

[54] DIAGNOSTIC TEST CARD

[75] Inventors: Stephen B. Friedman, 472 W. Mount Carmel Drive, Claremont, Calif. 91711; Carl B. Linnecke, 69 W. Winnie Way, Arcadia, Calif. 91006

[73] Assignee: Akzona Incorporated, Asheville, N.C.

[21] Appl. No.: 733,649

[22] Filed: Oct. 18, 1976

[51] Int. Cl.$^2$ .................. G01N 31/02; G01N 33/16
[52] U.S. Cl. ........................ 23/253 TP; 23/230 B; 23/259; 424/11; 424/12
[58] Field of Search .............. 23/230 B, 253 TP; 424/11, 12

[56] References Cited
U.S. PATENT DOCUMENTS

| | | | |
|---|---|---|---|
| 3,432,275 | 3/1969 | Unger | 424/11 X |
| 3,990,850 | 11/1976 | Friedman | 424/11 X |

*Primary Examiner*—Sidney Marantz
*Attorney, Agent, or Firm*—Francis W. Young; Robert H. Falk

[57] ABSTRACT

A test card adapted for the performance of an immunochemical diagnostic or serological test thereon comprises a test surface member and a covering member foldable thereon, the covering member being provided with circular convex windows which when folded over are in registry with circular test areas on the test surface member, permitting visual observation of test results, the inner surface of the covering member having adhered thereto a continuous sheet of an absorbent material which becomes transparent upon contact with a liquid, said sheet extending across the windows and permitting viewing of the test results when the test card is closed. Fixed to both surfaces of the absorbent material is a film of double sided adhesive. This adhesive covers the entire absorbent sheet on both sides except for cut-out areas in registry with the transparent window and reaction area. The adhesive on one side bonds the absorbent material to the cover element. On the other side it is bound to the absorbent material and covered by a peel-away element. This peel-away element is removed prior to attaching the cover element to the reaction bearing element. The card may be used, for example, for blood group typing.

11 Claims, 4 Drawing Figures

DIAGNOSTIC TEST CARD

BACKGROUND OF THE INVENTION

The present invention relates to a novel test card adapted for the performance of an immunochemical, diagnostic or serological test thereon, provided with means for permitting observation, protecting the user from contact with test reagents and sample, for preserving test results, and for attachment to a supporting surface.

In U.S. patent application Ser. No. 646,830, filed Jan. 6, 1976 now U.S. Pat. No. 3,990,850, there is described a test card for the afore-mentioned purposes comprising a card-shaped substrate material carrying dried test reagents on one side of the surface thereof, and having a foldable absorbent portion adjacent to the test reagents, forming a flap having openings in registry with a transparent window, so that when the flap is folded over onto the main body of the card, the window is in registry with the reagent areas, permitting viewing of the test area contents. This permits the entire card to be kept for record purposes, space being provided for inscribing record data.

Earlier versions of various types of test card which do not have the foregoing features are disclosed in U.S. Pat. Nos. 3,666,421, 3,770,383, 2,770,572, 3,074,853, and 3,502,437.

GENERAL DESCRIPTION OF THE INVENTION

In accordance with the present invention, there is provided a novel test card of the character described, having improved features described more fully below.

In accordance with a presently preferred embodiment, there is provided a test card adapted for the performance and preservation of blood group tests, and the invention will be described with reference thereto. However, it is to be understood that the discussion in regard thereto is for purposes of illustration only, and that the test card of the invention is adapted for a wide variety of immunochemical and diagnostic tests thereon, including, for example, human chorionic gonadotropin, rheumatoid factor, mononucleosis, and others.

The novel test card of the invention will be illustrated with respect to reagents for the performance of tests for A, B, AB and O blood groups.

The test card comprises a substantially plane strip of a substrate material providing a test surface member, and a covering member coextensive in area therewith and foldable upon said test surface member, permitting viewing and preservation of the test results. The substrate material, which may be, for example, treated or coated cardboard, has the test area surface substantially insoluble in, impermeable to, non-absorbent to, and wettable by water. The test portion carries on its test surface at least one circumscribed test area containing at least one deposited dried test reagent providing a predetermined amount thereof, which upon being moistened, e.g. with the liquid to be tested, is reconstituted to become the test reagent, and then united with the sample to be tested, forming an area of reaction mixture.

The covering portion of the test card, which may be either integral with the test portion and joined thereto along a fold line running transversely across the card, or which may be a separate member attached to the test portion by suitable hinge means, includes at least one transparent viewing window, forming a flap which is foldable along the fold line or the hinge, so that when folded over onto the face of the test portion, said window is in registry with said circumscribed test area, to permit viewing of the contents, and subsequent sealing and preservation of the test results. The underside of the test portion of the card is provided with means for the attachment of the entire card to a supporting surface, such as a record card or sheet of paper.

Fixed to both surfaces of the absorbent material is a film of double sided adhesive. This adhesive covers the entire absorbent sheet on both sides except for cut-out areas in registry with the transparent window and reaction area. The adhesive on one side bonds the absorbent material to the cover element. On the other side it is bound to the absorbent material and covered by a peel-away element. This peel-away element is removed prior to attaching the cover element to the reaction bearing element.

DESCRIPTION OF THE PREFERRED EMBODIMENT

The characteristics and method preparation and use of the test card of the invention will be better understood by reference to the accompanying drawings, which illustrate a presently preferred embodiment, but are not to be considered as limiting the invention thereto. In the drawings.

Figure 1:
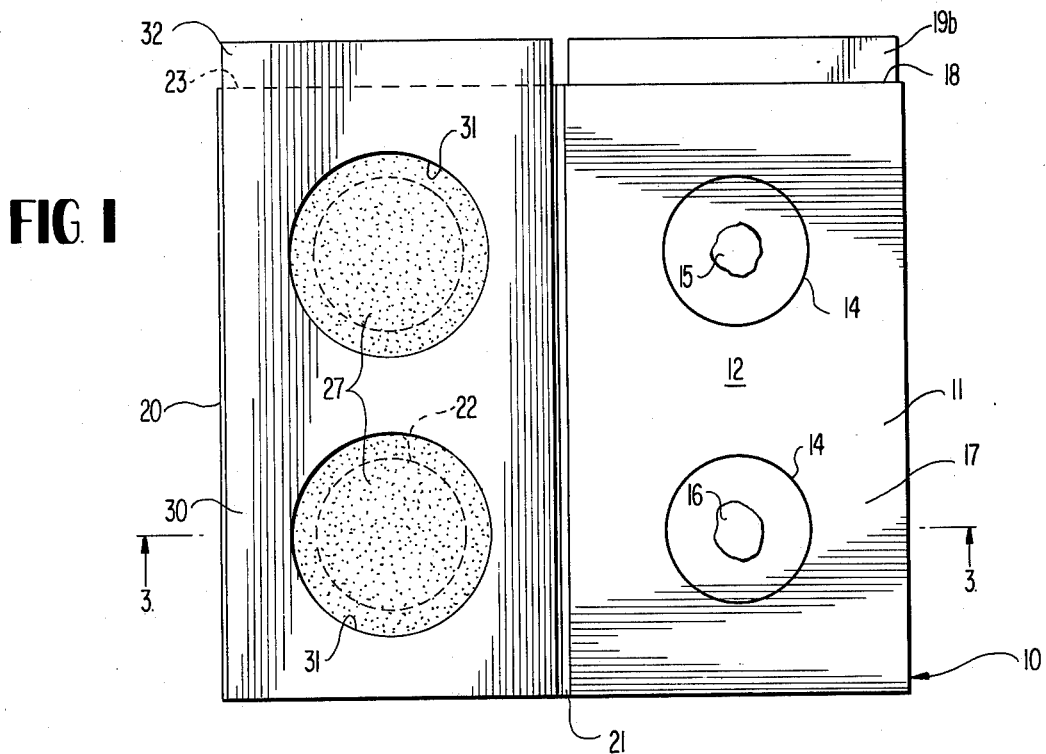
FIG. 1 is a plan view of the upper side of the open test card, showing test areas and window members.

Referring to the drawings, FIG. 1 shows a test card suited for the performance of a blood typing test for blood groups A, B, AB and O. The card 10 comprises a substantially rectangular sheet or strip of substrate material 11, e.g. cardboard, having the impermeability toward water and the wettability referred to above. The substrate may be glass, glazed porcelain, or a synthetic plastic material treated to make it wettable, but is preferably cardboard, having one or both surfaces coated with a coating 17 of vinyl resin or plasticized nitrocellulose. The coating should have a thickness which will maintain the flexibility of the cardboard, e.g. about 0.01–0.02 inch.

The test card 10 comprises two portions, namely a test surface 12, and a flap or covering portion 20 which is attached along line 21. The attachment may be by suitable hinge means, shown generally in the drawings. If the flap is integral, it will be capable of being folded over onto the test surface along fold line 21, which may be slightly scored or embossed into the card surface. The edge 18 of the test portion and the edge 23 of the flap portion are in alignment.

The test area 10 bears on its surface two circles 14 of contrasting color to the surface, which serve to demarcate the location of the area within which the test is performed. These circles 14 are located so as to be in alignment with the centers of the viewing windows 22 of the flap portion, as described below.

In the embodiment shown in FIG. 1 there are two test reagents. The first, designated 15 is a solid dried spot of Anti-B antiserum which when mixed with the blood of a person having the type of blood in Group B, will agglutinate. There is also a solid dried spot of Anti-A antiserum designated 16, which will similarly agglutinate the blood of a person belonging in blood group A.

The entire test card, in the embodiment shown, may be of a convenient size for record-keeping purposes, for example 3 × 3.5 inches when unfolded, and 3 × 1.75 inches when closed. The total fold card thickness may be about 0.03–0.06 inch when closed. The test reagents spots advantageously have an average diameter between about 5 and about 15 mm, and the circles 14 about 21 mm in diameter.

Joined to the body 11 of the test card is the covering or protective flap portion 20, being attached along line 21. Said flap portion, shown in open position in FIG. 1, and in cross-section in FIG. 2, is provided with convex windows 22, which are spaced apart from line 21 a distance such that when the flap portion is folded over onto the test area they will be in registry with the corresponding circular test areas 14, exposing the contents of the latter to view through windows 22.

Figure 2:
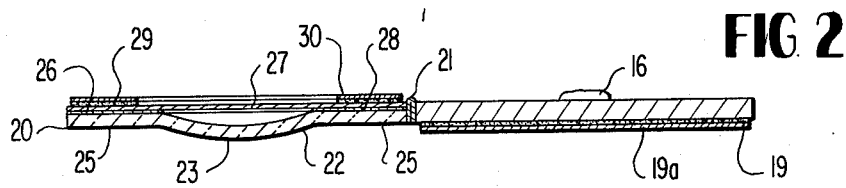
FIG. 2 is an enlarged cross-sectional view of the test card of FIG. 1, taken along the line 3 — 3.
Figure 3:
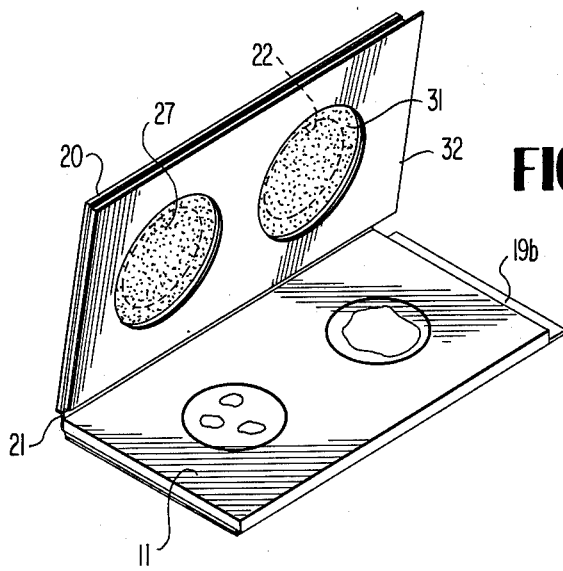
FIG. 3 is a view in perspective showing the partly folded test card and various features thereof.

As shown in FIGS. 2 and 3, the underside of test portion 11 is coated with a layer 19 of adhesive material, namely a pressure-sensitive adhesive of any suitable type, upon which there is mounted a layer of peelable or strippable material 19a, such as waxed paper, or plastic film, which has a tab portion 19b which extends beyond edge 18 of the test portion to permit grasping of the strippable member for removal. Removal thereof exposes the adhesive layer 19 which can then be used to mount the test card upon any desired surface.

The construction of the flap portion 20 will be more readily understood by reference to FIG. 2. The boundary adjacent to the test portion is either formed by fold line 21, or constitutes the edge of the flap member. In the preferred embodiment shown, the latter forms a separate structure attached by suitable hinge means, shown generally.

The flap portion 20 is preferably formed of a rectangular piece of thin rigid plastic material, for example, polyethylene, provided with two transparent windows 22 which are convex in shape and extend outwardly as shown at 23.

This convex configuration is for the dual purposes of providing strength, and protecting the test agglutinates against injury when the flap is closed. The area surrounding the transparent windows of the plastic member may be colored with an opaque contrasting color, such as blue, to enhance the visibility of the test display.

As shown in FIGS. 2 and 3, there is adhesively mounted on the inner face 26 of the flap portion, a continuous thin sheet of an absorbent material 27, such as treated tissue paper or the like, which extends across the windows 22, and which will become transparent on contact with a liquid. The wet agglutinates formed in the performance of the tests upon portion 11 have a tendency to be mobile on the wet card surface and to migrate to the edges of the test areas.

The absorbent sheet 27, when the flap or covering member is folded over onto the reaction bearing test surface and upon contact with the reaction mixture, becomes transparent, permitting visual observation of the test results.

The absorbent sheet 27 is a "tea bag" type material, 0.002–0.005 ins. thick, partially translucent, highly absorbent, and with good wet tear strength. Although partially translucent, the fibers of the sheet block and scatter light passing through thus destroying the image of anything viewed through the material. When wetted, the fibers absorb reaction fluid (Serum $H_2O$) and transmit light coherently maintaining the image of objects viewed through the material. Since the absorbent sheet 27 is a continuous web, it immobilizes the agglutinates much like a net, while allowing for diffusion and an increased liquid-to-air interface. This diffusion phenomenon hastens the drying time, but at the same time, diffusing reaction liquid is prevented from reaching an exposed edge by the dimensions of the absorbent material. The convex windows 22 prevent compression or disruption of the agglutination reaction product by providing an air layer between the window bubble 23 and the absorbent material 27.

The absorbent sheet 27 is attached to the inner surface of the flap member 20 by a layer 28 of adhesive. On the opposite face of the absorbent sheet 27 there is a coating 29 of a pressure-sensitive adhesive of any suitable type, upon which is mounted a sheet of peelable or strippable material 30, which is provided with circular openings 31 which are concentric with windows 22 but of slightly greater diameter. The pressure-sensitive adhesive coating 29 is applied in such manner as to leave uncoated the areas defined by circular openings 31. The peelable member 30 has a portion 32 which extends beyond the outer edge of the flap to permit grasping of the member for removal and exposure of the adhesive. Upon removal, the flap or cover member may be folded over onto the test portion 11 and adhered thereto.

The resulting closed test card is a compact and strong permanent recording device. The viewing areas provided by the windows in the covering element in registry with the reaction area permit observation of the test results whenever desired. The action of the absorbent sheet 27 absorbs excess reaction mixture and leaves the agglutinates present and clearly visible in the observation area. Diffusion of the reaction mixture does not reach the edges of the card, but air can permeate to dry the reaction products. The latter are protected from disruption by the cover element which incorporates the convex viewing means for added strength. The reaction products and test results are kept isolated from human contact and possible infection by outside sources. The sealed test results can readily be stored and held for future reference and interpretation.

Figure 4:
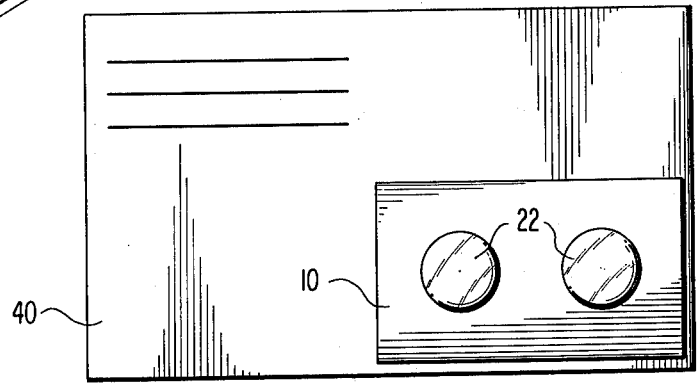
FIG. 4 is a plan view of a record card having the closed test card attached thereto, with visible test results.

The perspective view of FIG. 3 shows the test card assembly ready for closure, with the test areas on test portion 11, and the windows 22 covered by the sheet of absorbent material on the inner face of the cover member. When the test is completed, the card is closed, the peelable layer is removed from the underside of the card and the closed device is affixed to a donor history card, as shown in FIG. 4. Alternatively the test card can be affixed to the donor history card first, the test performed and the card closed and seal in situ.

The manner of using the test card of the invention will be illustrated with respect to the performance of a blood group test, but this is not to be considered as limiting the invention thereto.

The test card is first prepared with test reagent 16 being a solid dried spot of antiserum of blood group B, and with reagent 15 being a solid dried spot of antiserum of blood group A. The preparation of these sera is well known and can be carried out, for example, as described in U.S. Pat. No. 2,770,572.

The test card with said reagents in the respective circles on the surface facing the user, is placed horizontally with the cover member open. The tests may be performed with the test card attached to a donor record by removal of the strippable layer from the bottom of the test portion.

With the test card in the aforementioned position, one drop of distilled water (approximately 0.03 ml) is placed on top of each spot of test antiserum, to reconstitute the reagents. Then a volume of blood to be tested, equal to approximately ¼ to ½ of the distilled water volume applied previously, is placed next to each reagent test spot, e.g. The first reagent (Anti-A) is reconstituted by stirring the water into it with a stirrer, e.g. a toothpick, until thoroughly mixed. Then the blood sample is stirred into the reconstituted reagent using the same stirrer (e.g. same end of toothpick) and the reaction mixture is spread to cover the entire area of the circumscribed circle. Next the other spot B is reconstituted with water and mixed with blood to be tested in the same manner as spot A, using clean stirrers, (e.g. opposite end of toothpick).

Thereafter the test card is rocked gently for about 2 minutes, in which time the reactions on the card will be seen.

If agglutination takes place only in test area of Anti-A, the blood sample is group A. If agglutination takes place in only test area of Anti-B, the blood sample is group B. If agglutination occurs in both test areas, the blood is group AB. If no agglutination takes place, the blood is that of group O.

At the end of two minutes, the card is placed on a horizontal flat surface, the strippable paper on the inner side of the covering member is removed and the cover folded over and adhered to the test surface member. This results in a covered closed device within which the test results are sealed and may be preserved and filed, and are protected from environmental injury. The donor card may be used to record additional information and is adapted for storage in standard filing systems.

What is claimed is:

1. A closable test card for performing immunochemical diagnostic or serological tests on the surface thereof, comprising:
   a. a test surface member comprising a substantially plane strip of a substrate material having a test surface which is substantially insoluble in, impermeable to, nonabsorbent to, and wettable by aqueous media;
   b. a covering member coextensive in the area with said test surface member and foldable thereupon to permit preservation and visual observation of test results;
   c. said test surface carrying at least one circumscribed test area containing at least one deposited dried reagent providing a predetermined amount of a test reagent, which upon being moistened is reconstituted to said reagent;
   d. said covering member being joined to said test surface member and foldable thereover to form a closed test card, and including at least one area provided with a transparent convex viewing window, said area being positioned in such manner that when said covering member is folded over onto said test surface member said area and transparent window are in registry with said test reaction area, permitting viewing of the test area contents;
   e. said covering member having adhered to the inner surface thereof a continuous sheet of an absorbent material which becomes transparent upon contact with a liquid, said sheet extending across said window area, permitting viewing of the test results through said windows when the test card is closed.

2. The test card of claim 1 which has a layer of an adhesive on the side of the test surface member opposite to the test area for attachment of the test card to a supporting surface.

3. The test card of claim 1 in which said test areas are circular in configuration.

4. The test card of claim 1 in which said areas in said covering member are circular in configuration and approximately of the diameter of the test areas which are also circular in configuration.

5. The test card of claim 1 which further includes a coating of an adhesive on the outer surface of said sheet of absorbent material except on those sheet portions extending across said window areas.

6. The test card of claim 5 in which said coating of adhesive is covered by a sheet or film or strippable material.

7. The test card of claim 2 in which said coating of adhesive on the underside of said test surface member is covered by a sheet or film of strippable material.

8. The test card of claim 1 in which said covering member is formed of thin rigid plastic material.

9. The test card of claim 1 in which said covering member is hinged to said test surface member.

10. The test card of claim 1 in which there are two test areas on said test surface, each enclosing a dried spot of blood groups antiserum test reagent.

11. A recording system comprising a record card having attached to its surface the test card according to claim 1.

* * * * *